United States Patent [19]

Stenkvist

[11] 4,435,507

[45] Mar. 6, 1984

[54] PROCESS AND DEVICE FOR PREPARATION OF CELL SAMPLES FOR CYTOLOGICAL TESTS

[76] Inventor: Björn G. Stenkvist, Döbelnsgatan 13, S-752 37 Uppsala, Sweden

[21] Appl. No.: 355,588

[22] PCT Filed: Jun. 30, 1981

[86] PCT No.: PCT/SE81/00199
§ 371 Date: Feb. 18, 1982
§ 102(e) Date: Feb. 18, 1982

[87] PCT Pub. No.: WO82/00200
PCT Pub. Date: Jan. 21, 1982

[30] Foreign Application Priority Data

Jul. 8, 1980 [SE] Sweden ............................... 8005023

[51] Int. Cl.³ .................. C12Q 1/36; C12Q 1/42; A01N 1/02
[52] U.S. Cl. .................. 435/262; 435/2; 435/24; 436/63; 436/177; 436/8; 424/3; 210/927
[58] Field of Search ........... 210/927; 436/63, 177, 436/178, 8, 10, 16; 435/218, 22, 24, 262; 424/3

[56] References Cited

U.S. PATENT DOCUMENTS 3,206,128 9/1965 MacPherson et al. .............. 241/26
3,779,371 12/1973 Rovinski ........................... 206/222
3,870,639 3/1975 Moore et al. ..................... 210/927 X

FOREIGN PATENT DOCUMENTS 1084886 7/1960 Fed. Rep. of Germany .
1617894 4/1971 Fed. Rep. of Germany .
1034462 7/1972 Fed. Rep. of Germany .
2627416 1/1977 Fed. Rep. of Germany .
2703326 10/1977 Fed. Rep. of Germany .
401107 8/1972 Sweden .

OTHER PUBLICATIONS

Patent Abstracts of Japan, abstract of JP 52-113793 published Sep. 24, 1977, Hitachi Seisakusho K.K.

*Primary Examiner*—Ferris H. Lander
*Attorney, Agent, or Firm*—Stevens, Davis, Miller & Mosher

[57] ABSTRACT

Process for preparing cell samples for cytological tests of exfoliated cells, in which the cell sample is in the form of a slurry in a physiological solution, which is introduced into a first chamber (5) provided with a wall (2) with a large number of holes with a cross section of 10–100 μm and communicating with a second chamber (6). The solution is pressed under the influence of a pressure differential between the first (5) and the second (6) chamber through the wall (2) with holes. The material for the cell sample is taken from the solution in the second chamber (6) for smearing on a slide. A suitable device for carrying out the process is also described.

8 Claims, 1 Drawing Figure

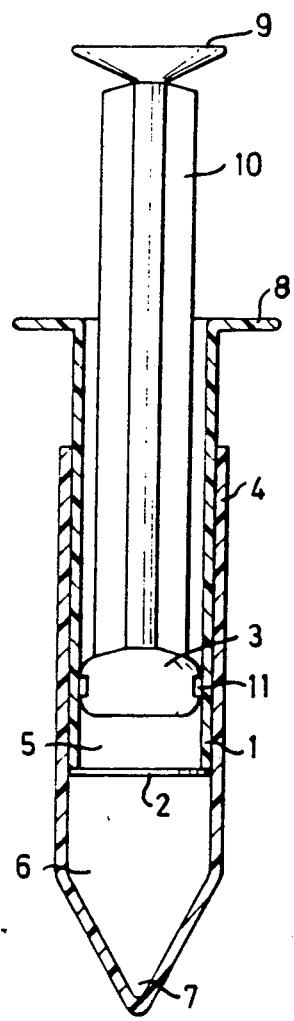

PROCESS AND DEVICE FOR PREPARATION OF CELL SAMPLES FOR CYTOLOGICAL TESTS

The present invention relates to a process for preparation of cell samples for cytological tests of exfoliated cells, and a device for carrying out the process.

Cytological tests of cell samples are now quite prevalent and have proved to be an exceptional means for diagnosing cell changes in the area about the portio-cervix and endocervical canal. Such tests are performed on large numbers of women and not infrequently on entire age groups of women within a district for example.

There are also tests of cell samples taken from other portions of the body done regularly at the cytological laboratories, but not other test is as frequently done as the cervical smear. A cell sample taken from the cervical canal reveals cell changes with a reliability of about 95%, and of these 20–25% are precancerous. A positive response to the cell change test usually results in an operation, a so-called scraping or use of a cone instrument. The results of such treatment are good and well warrant extensive testing of healthy women in certain age groups.

The samples are taken with a curette or similar instrument by scraping cells from the mouth of the cervix. It is of course very important that any cell changes be represented in the sample. There are a number of different types of sampling devices which provide acceptable samples. The samples are taken by inserting a speculum into the vagina whereafter the sampling instrument is inserted and the scraping is done.

The sample material must then be protected from destruction while being transported to the cytological laboratory, suitably by immersion in a fixing solution.

After the sample has arrived at the laboratory it is prepared by dyeing and is inspected in a microscope. The presence of atypical cells is noted and reported. The examination under the microscope and the evaluation requires exceptional attentiveness and is time-consuming, and is considered to be quite demanding work. In 1980 each test cost between 50 and 100 Swed.Kronor.

Consequently, intensive development work is in progress to simplify and make less expensive sampling, sample preparation and sample evaluation. In order to simplify the evaluation of the samples under the microscope, a number of systems have been developed for automatic evaluation of cells as normal or atypical. Algorithms have been formulated for automatic evaluation and the development of commercial systems is fairly far along.

It is thus possible with reasonably good accuracy to determine if atypical cells are present in a cell sample, if the cell sample has been prepared so that a substantial portion of the cells are free cells on the slide. Under certain conditions, a human evaluator can also recognize atypical cells in clumps of cells, however.

This is not the case with automatic examination of a cell sample and thus it is of crucial importance in this case to have as many free cells as possible. Samples have been prepared previously with a conventional syringe, for example, provided with a cannula with a diameter of 500 μm, by alternatingly sucking up and expelling the slurry of scraped cells. This produced cell samples which could be read by an experienced human examiner. In order to be read automatically, the sample preparation must be improved so that the majority of the cells in the sample are free cells.

The purpose of the present invention is thus to provide an effective process for sample preparation of cell samples and a device for carrying out the process.

The new process is essential for establishing a functioning system for automatic cell testing and facilitating substantially the non-automated evaluation of cell samples.

The new process, intended for the preparation of cell samples for cytological testing of exfoliated cells, in which the cell sample is in the form of a slurry in a fixing solution, is characterized in that the slurry is introduced into a first chamber provided with a wall with a large number of holes with a cross section of 10–100 μm and in communication with a second chamber and that said solution, under the influence of a pressure differential, is made to pass through the wall provided with holes one or more times, and that the material from the second chamber is used for the preparation of smears on a slide.

It is preferable that the cross section of the holes being 10–40 μm. If the cross section is less than 5 μm, the results will not be reproducible, and if the cross section is more than 100 μm, the results of the test preparation will be less than satisfactory.

After one or more passages through the wall provided with holes, the solution is allowed to settle in the second chamber and a smear on a slide is made from the sedimented material.

It has been shown to be suitable to use a pressure differential between the first and the second chambers of 50–1000 kPa to press the slurry through the wall provided with holes.

The pressure differential is suitably established by pressing a plunger into a cylindrical cavity, said cavity communicating with the first chamber.

The slurry suitably contains a cell dissociating agent, which can be for example hyaluronidase, chymotrypsin or 1,4-dimercapto-2,3-butane diol. Fixing agent, such as 50–95% ethanol is also included and suitably also a small amount of sodium hydroxide.

A device for carrying out the new process consists of a first and a second chamber separated by a wall, provided with a large number of holes with a cross section of 10–100 μm. It is also provided with means for establishing a pressure differential between the first and the second chamber. Furthermore, it is arranged to make it possible to introduce slurry into the first chamber and to extract finished, possibly sedimented sample material from the second chamber. The device can consist of a first tube, closed at one end and into which a second tube has been partially inserted, which at its inserted end is provided with a large number of holes and is essentially sealingly connected to the first tube. A movable plunger is arranged in the second tube and can be moved reciprocally there. Said plunger can also be inserted and removed from the second tube for introducing the slurry into the second tube.

A preferred embodiment of the invention will be described in more detail with reference to the accompanying drawing.

The device consists of three parts: a tube 1 provided with a wall 2 with a plurality of holes, a plunger 3 and an outer closed tube 4. The tube 1 with the wall 2 and the plunger 3 defines the first chamber 5. The tube 1 can be inserted into the outer tube 4 suitably so as to seal against each other. The second chamber 6 is defined in the tube 4 by the lower end of the closed tube and the wall tube provided with holes. The outer tube 4 is suitably a centrifuge tube with a pointed lower end 7. The tube 1 and the plunger 3 are suitably made as a hypodermic syringe with a flange 8 and a pressing surface 9 as well as wings 10 for centering the movement of the plunger in the tube 1 when pressure is exerted on the pressure surface 9. The plunger 3 is suitably provided with a rubber packing 11 to provide a better seal between the plunger 3 and the tube 1.

The device shown is intended for manual sample preparation, the plunger 3 first be removed from the tube 1 and the sample slurried in the physiological fluid being poured down into the tube 1. The plunger 3 is inserted and then pressed down through the tube 1. The solution will then be pressed through the wall with holes, suitably represented by a wire-mesh or a net of artificial fibers with a cross section diameter of 10-100 $\mu$m. The tubes 1 and 4 can then be turned over and the plunger 3 drawn out, thereby sucking the solution through the wall with holes, whereafter the liquid is again pressed with the plunger through the wall with holes. The process is suitably repeated a number of times, whereafter the liquid is sedimented or centrifuged in the tube 4. The material for the smear can then be taken from the sedimental material thus providing a smear which has free cells to a large degree and which is suitable for automatic evaluation.

The person skilled in the art should have no difficulty conceiving automatic units in which the sample preparation can be done completely automatically even if we have not described here an example of such a device.

I claim:

1. Process for preparation of cell samples for cytological tests of exfoliated cells, in which the cell sample is in the form of a slurry in solution, characterized in that the slurry is introduced into a first chamber provided with a wall with a large number of holes with a cross section of 10-100 $\mu$m and in communication with a second chamber, and that said solution under the influence of a pressure differential between the first and the second chambers is made to pass through the wall provided with holes one or more times, and that the material from the second chamber is used for the preparation of smears on a slide.

2. Process according to claim 1, characterized in that the cross section of the holes is 10-40 $\mu$m.

3. Process according to claim 1, characterized in that a pressure differential of 50-1000 kPa is used to press the slurry through the wall provided with holes.

4. Process according to claim 1, characterized in that the liquid is allowed to sediment in the second chamber and that smears are made from the sediment material.

5. Process according to claim 1, characterized in that the pressure differential is established by pressing a plunger into a cylindrical cavity, said cavity being in communication with the first chamber.

6. Process according to claim 1, characterized in that the slurry contains a cell dissociating agent and a fixing agent.

7. Process according to claim 6, characterized in that the cell dissociating agent consists of hyaluronidase, chymotrypsin or 1,4-mercapto-2,3-butane diol and the fixing agent of 50-95% ethanol and that the slurry contains a small amount of sodium hydroxide.

8. Process according to claim 1, characterized in that the slurry is made to pass through the wall by alternating pressure and suction effect.

* * * * *